United States Patent
Kobayashi et al.

(10) Patent No.: US 8,469,718 B2
(45) Date of Patent: Jun. 25, 2013

(54) SENSOR APPARATUS HAVING A SENSOR CONNECTED TO A CIRCUIT BOARD CONNECTED TO EXTERNAL TERMINALS

(75) Inventors: Akihiro Kobayashi, Nisshin (JP); Shingo Yoshida, Ichinomiya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 13/327,871

(22) Filed: Dec. 16, 2011

(65) Prior Publication Data

US 2012/0164850 A1     Jun. 28, 2012

(30) Foreign Application Priority Data

Dec. 17, 2010  (JP) ................................ 2010-281191

(51) Int. Cl.
*H01R 13/60*   (2006.01)
*G01M 15/10*  (2006.01)

(52) U.S. Cl.
USPC .......................................... 439/55; 73/23.31

(58) Field of Classification Search
USPC ... 439/352–358, 55, 557, 488–490; 73/23.31, 73/723, 715
See application file for complete search history.

(56) References Cited

U.S. PATENT DOCUMENTS

| | | | |
|---|---|---|---|
| 6,132,256 A | 10/2000 | Morsdorf et al. | |
| 6,547,955 B1 | 4/2003 | Hada et al. | |
| 6,652,293 B2 * | 11/2003 | Fuchs et al. | 439/76.1 |
| 6,814,616 B2 | 11/2004 | Pade | |
| 6,849,174 B2 | 2/2005 | Hada et al. | |
| 7,901,219 B2 * | 3/2011 | Sakiyama et al. | 439/76.2 |
| 8,286,496 B2 * | 10/2012 | Sekiya et al. | 73/723 |
| 2002/0111071 A1 | 8/2002 | Pade | |
| 2003/0162440 A1 | 8/2003 | Pade | |
| 2011/0061443 A1 * | 3/2011 | Minami et al. | 73/23.31 |
| 2012/0315772 A1 * | 12/2012 | Joschika | 439/55 |

FOREIGN PATENT DOCUMENTS

| | | | |
|---|---|---|---|
| JP | 59-170723 A | 9/1984 | |
| JP | 2-61546 A | 3/1990 | |
| JP | 2-259459 A | 10/1990 | |
| JP | 2000-502454 A | 2/2000 | |
| JP | 2000-171435 A | 6/2000 | |
| JP | 2004-519691 A | 7/2004 | |
| JP | 2005-315757 A | 11/2005 | |
| JP | 2007-93508 A | 4/2007 | |
| JP | 2007-93508 A | 4/2007 | |

OTHER PUBLICATIONS

Japanese Office Action dated Mar. 19, 2013 for corresponding Japanese Patent Application No. 2011-273414.

* cited by examiner

*Primary Examiner* — Chandrika Prasad
(74) *Attorney, Agent, or Firm* — Sughrue Mion, PLLC

(57) ABSTRACT

A sensor apparatus (10) including a sensor (20), a cable (80), a circuit board (50) and a housing (30) accommodating the circuit board. The housing (30) includes a first member (100) and a second member (200). The first member (100) supports the circuit board (50) in such a condition that the circuit board (50) is electrically connected to an external terminal (40). The second member (200) receives the cable (80) inserted thereinto and is engaged with the first member (100), thereby accommodating the circuit board (50) in cooperation with the first member (100). As a result of engagement between the first member (100) and the second member (200), the housing (30) establishes an electric connection of the circuit board (50) to the cable (80).

12 Claims, 17 Drawing Sheets

SENSOR APPARATUS HAVING A SENSOR CONNECTED TO A CIRCUIT BOARD CONNECTED TO EXTERNAL TERMINALS

TECHNICAL FIELD

The present invention relates to a sensor apparatus having a sensor and particularly to a sensor apparatus in which a circuit board for driving a sensor is connected to the sensor through a cable.

BACKGROUND ART

A known sensor apparatus in which a circuit board is connected to a sensor through a cable detects the concentration of a particular gas component, such as oxygen or nitrogen oxides, by means of the sensor, and outputs an electric signal generated on the basis of the detection result from the sensor, to an external system from the circuit board (refer to, for example, Patent Documents 1 to 3). The circuit board of the sensor apparatus is generally accommodated within a housing so as to be protected from impact, water, and dust.

PRIOR ART DOCUMENTS

Patent Documents

[Patent Document 1] Japanese Patent Application Laid-Open (kokai) No. S59-170723
[Patent Document 2] Japanese Patent Application Laid-Open (kokai) No. 2000-171435
[Patent Document 3] Japanese Patent Application Laid-Open (kokai) No. 2007-93508

SUMMARY OF THE INVENTION

Problems to be Solved by the Invention

Conventionally, a process of manufacturing a sensor apparatus has failed to sufficiently consider workability in accommodating the circuit board into the housing.

In view of the above problem, an object of the present invention is to improve workability in a process of manufacturing a sensor apparatus.

Means for Solving the Problems

The present invention has been achieved to at least partially solve the above problem and can be embodied in the following modes or application examples.

[Application example 1] A sensor apparatus of application example 1 comprises a sensor; a cable electrically connected to the sensor; a circuit board electrically connected to the sensor through the cable, drivingly controlling the sensor, and outputting an electric signal generated on the basis of detection result from the sensor; and a housing accommodating the circuit board. The housing comprises a first member and a second member. The first member has an external terminal for allowing an external system to be electrically connected to the circuit board and supports the circuit board in such a condition that the circuit board is electrically connected to the external terminal. The second member receives the cable inserted thereinto; is engaged with the first member; and accommodates the circuit board in cooperation with the first member. As a result of engagement between the first member and the second member, the housing establishes an electric connection of the circuit board to the cable. According to the present application example, the first member and the second member are engaged with each other, thereby accommodating the circuit board in the housing and at the same time establishing an electric connection of the cable to the circuit board. As a result, workability in a process of manufacturing the sensor apparatus can be improved.

[Application example 2] The sensor apparatus of application example 1 may be configured as follows: the first member has a first terminal electrically connected to the circuit board and allowing the sensor to be electrically connected to the circuit board; the second member has a second terminal electrically connected to the cable and being engageable with the first terminal; and as a result of engagement between the first member and the second member, the first terminal and the second terminal are engaged with each other and electrically connected to each other. According to the present application example, electrical connections can be readily established merely through engagement between the first member and the second member without involvement of a complex housing structure.

[Application example 3] The sensor apparatus of application example 2 may be configured as follows: the first terminal and the second terminal, together with the circuit board, are sealed in the housing in a condition that the first member and the second member are engaged with each other. According to the present application example, similar to the circuit board, the first terminal and the second terminal can be protected.

[Application example 4] The sensor apparatus of application example 2 or 3 may be configured as follows: the first terminal and the second terminal are disposed along a surface of the circuit board in a condition that the first member and the second member are engaged with each other. According to the present application example, the size of the housing can be reduced.

[Application example 5] The sensor apparatus of application example 2 may be configured as follows: the sensor apparatus further comprises a terminal block which holds the external terminal and the first terminal, and the terminal block is locked into engagement with the first member, whereby the external terminal and the first terminal are provided in the first member. According to the present application example, as compared with the case where the external terminal and the first terminal are integrally molded to the first member, workability in manufacture of the sensor apparatus can be improved. For example, when the specifications (material, plating, shape, quantity, etc.) of the external terminal and the first terminal are to be changed, such a change can be made through replacement of the terminal block rather than through replacement of the entire first member. Also, when moisture-proof coating is to be applied to the external terminal and the first terminal together with the circuit board, moisture-proof coating can be applied in a condition that these members are separated from the first member. Also, when the external terminal and the first terminal are to be soldered to the circuit board, soldering can be performed in a condition that these members are separated from the first member.

[Application example 6] The sensor apparatus of application example 5 may be configured as follows: the first member comprises two protrusions, each provided in a protruding condition and having a proximal end portion and a distal end portion; the terminal block is held between the two protrusions; and spacing between the two protrusions is narrower on a side toward the proximal end portions than on a side toward the distal end portions. According to the present application example, while attachment of the terminal block to the first member is facilitated, accuracy can be improved in positioning the external terminal relative to the first member.

[Application example 7] The sensor apparatus of application example 5 or 6 may be configured as follows: the terminal block is fixed to the circuit board, and the first member further comprises two board guide portions provided in a protruding condition and adapted to guide the circuit board therebetween. According to the present application example, the circuit board can be mounted to the first member without hindering the positioning of the external terminal relative to the first member.

[Application example 8] The sensor apparatus of any one of application examples 5 to 7 may be configured as follows: the terminal block comprises an external-terminal-side terminal block for holding the external terminal, and a first-terminal-side terminal block configured as a separate member from the external-terminal-side terminal block and adapted to hold the first terminal. According to the present application example, when the specifications (material, plating, shape, quantity, etc.) of either of the external terminal and the first terminal are to be changed, such a change can be made through replacement of either the external-terminal-side terminal block or the first-terminal-side terminal block.

[Application example 9] The sensor apparatus of any one of application examples 2 to 4 may be configured as follows: the external terminal and the first terminal are integrally molded to the first member. According to the present application example, a work step of individually attaching the external terminal and the first terminal to the first member can be eliminated.

[Application example 10] The sensor apparatus of any one of application examples 2 to 4 and 9 can be configured as follows: the first member comprises two board support portions provided in a protruding condition and adapted to support the circuit board therebetween, and a terminal support portion provided between the two board support portions in a bridging condition and adapted to support the first terminal. According to the present application example, while sufficient mounting rigidity is ensured in mounting the circuit board and the first terminal to the first member, the size of the housing can be reduced.

[Application example 11] The sensor apparatus of application example 10 may be configured as follows: the two board support portions have respective guides for guiding the second member to a position of engagement with the first member. According to the present application example, workability can be improved in engaging the first member and the second member with each other.

[Application example 12] The sensor apparatus of any one of application examples 1 to 11 may be configured as follows: the second member is a container body that functions as an opened container, and the first member is a lid body that functions as a lid of the second member. According to the present application example, workability can be improved in mounting the circuit board to the first member without impairment in protection of the circuit board by the housing.

Modes for carrying out the present invention are not limited to a sensor apparatus. For example, the present invention can be applied to various other modes, such as components of the sensor apparatus and a method of manufacturing the sensor apparatus. Also, the present invention is not limited to the above-mentioned modes, but may be embodied in various other modes without departing from the gist of the invention.

MODES FOR CARRYING OUT THE INVENTION

In order to further bring out the above-mentioned configurations and actions of the present invention, a sensor apparatus to which the invention is applied will be described.

A. First Embodiment

A-1. Configuration of Sensor Apparatus

Figure 1:
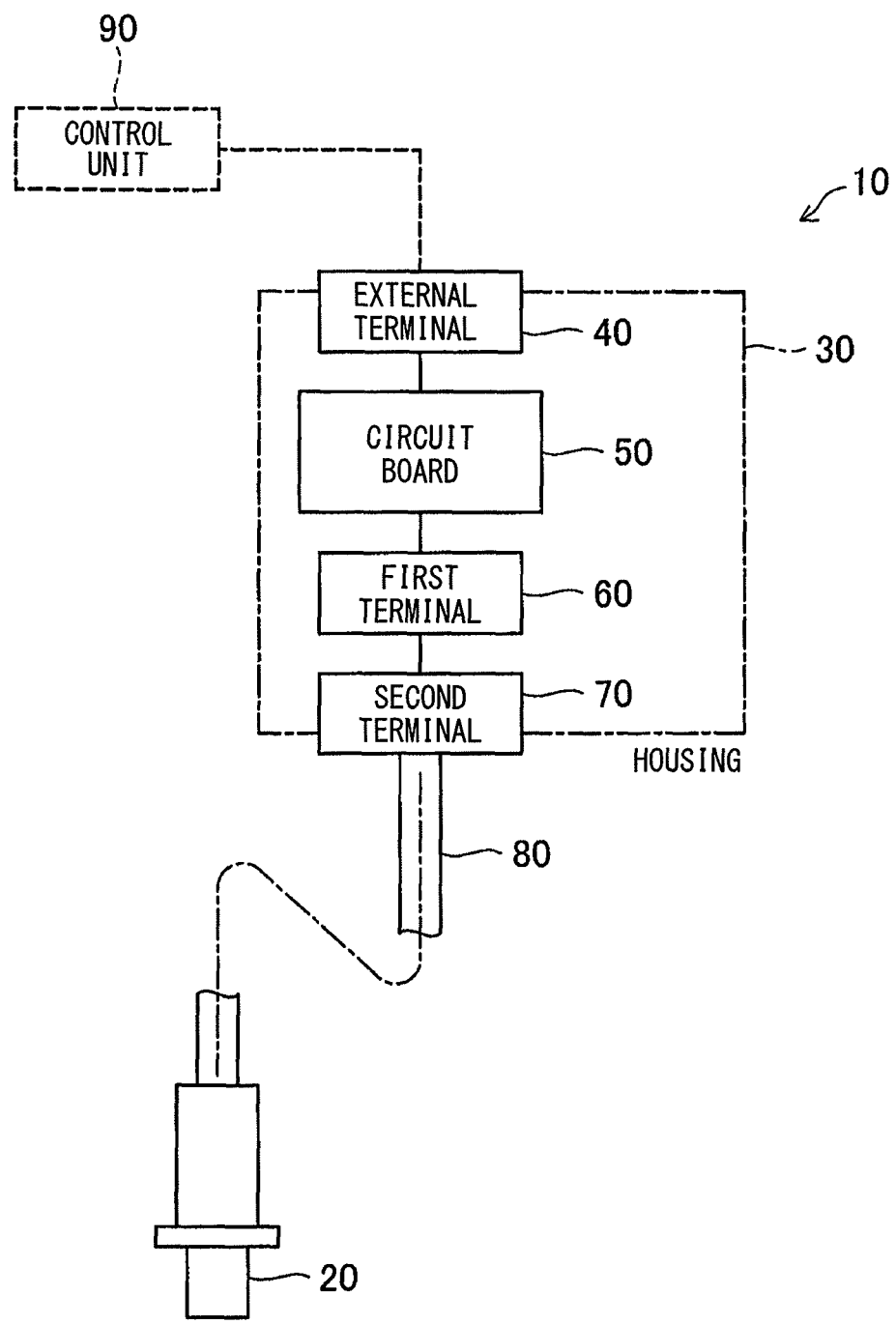
FIG. 1 Explanatory view showing the configuration of a sensor apparatus.

FIG. 1 is an explanatory view showing the configuration of a sensor apparatus 10. The sensor apparatus 10 includes a sensor 20, a housing 30, external terminals 40, a circuit board 50, first terminals 60, second terminals 70, and a cable 80. The sensor apparatus 10 can be electrically connected to an external system; i.e., a control unit 90, through the external terminals 40, and outputs an electric signal generated on the basis of the detection result from the sensor 20, to the control unit 90 through the external terminals 40. In the present embodiment, the sensor 20 is an oxygen ($O_2$) sensor which is provided in an exhaust pipe of an internal combustion engine and adapted to detect oxygen concentration in exhaust gas. The control unit 90 controls the internal combustion engine on the basis of oxygen concentration in exhaust gas.

The sensor 20 of the sensor apparatus 10 has such a publicly known configuration that a gas sensor element is accommodated within a housing. In the present embodiment, the gas sensor element of the sensor 20 is a plate-like element configured such that an oxygen pump cell composed of a solid electrolyte body and a pair of electrodes formed on the solid electrolyte body, an oxygen concentration detection cell composed of a solid electrolyte body and a pair of electrodes formed on the solid electrolyte body, and a heater for heating these cells are laminated together. The cable 80 is connected to the gas sensor element of the sensor 20 via metal terminals, etc., thereby establishing electric connection between the sensor 20 and the cable 80.

The circuit board 50 of the sensor apparatus 10 drivingly controls the sensor 20 and outputs, to the control unit 90, an electric signal generated on the basis of the detection result from the sensor 20. Specifically, the circuit board 50 (more specifically, the circuit board 50 on which circuit components are mounted) controls the magnitude and flow direction of current flowing to the oxygen pump cell, in such a manner that the electrode-to-electrode voltage of the oxygen concentration detection cell of the gas sensor element of the sensor 20 assumes a fixed value; detects current flowing to the oxygen pump cell through a detection resistor, thereby detecting oxygen concentration in exhaust gas; and outputs an electric signal indicative of information about oxygen concentration to the control unit 90. The circuit board 50 is electrically connected to the sensor 20 via the first terminals 60, the second terminals 70, and the cable 80 and is electrically connected to the control unit 90 via the external terminals 40. The circuit board 50 operates through energization by electric power supplied via the external terminals 40.

The cable 80 of the sensor apparatus 10 provides an electric junction between the sensor 20 and the circuit board 50. One end portion of the cable 80 is connected to the sensor 20, and the other end portion of the cable 80 is inserted into the housing 30.

The housing 30 of the sensor apparatus 10 accommodates the circuit board 50 therein and protects the circuit board 50 from impact, water droplets, dust, etc. The housing 30 has, in addition to the circuit board 50, the external terminals 40, the first terminals 60, and the second terminals 70 provided therein. In the present embodiment, the housing 30 also functions as a connector for physically and electrically connecting the sensor 20 to the control unit 90.

Figure 2:
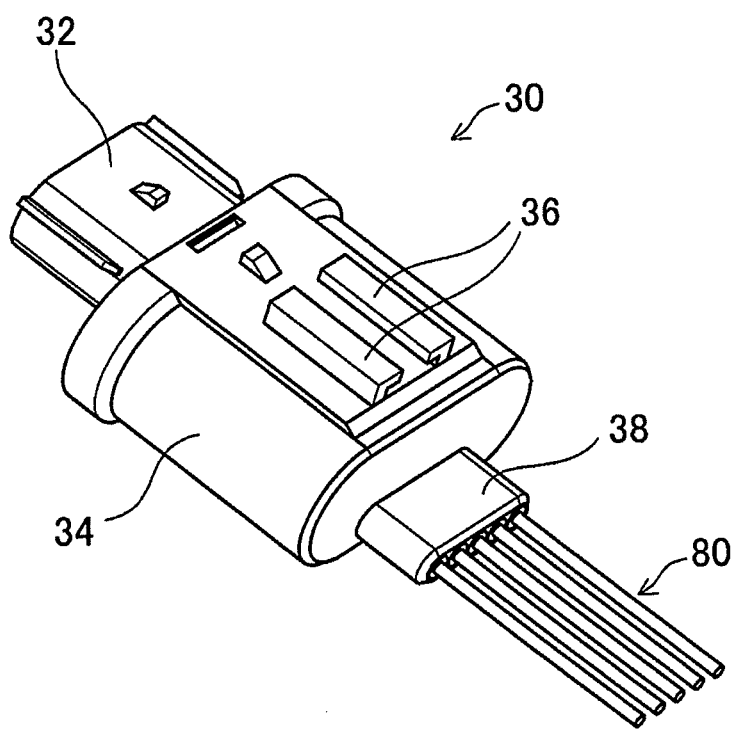
FIG. 2 Perspective view showing the detailed configuration of a housing.

FIG. 2 is a perspective view showing the detailed configuration of the housing 30. The housing 30 of the sensor apparatus 10 includes an external connector 32, a trunk portion 34, an engagement portion 36, and a cable insertion portion 38. The engagement portion 36 of the housing 30 is engageable with another member (not shown). The housing 30 can be fixed in position by use of the engagement portion 36.

The external connector 32 of the housing 30 allows the control unit 90 to be electrically connected to the circuit board 50. Through engagement with a connector (not shown) associated with the control unit 90, the external connector 32 maintains electrical connection to the control unit 90 through the external terminals 40. In the present embodiment, the external connector 32 is provided in a protruding condition at the end of the trunk portion 34 and surrounds the external terminals 40 protruding from the trunk portion 34.

The trunk portion 34 of the housing 30 is a hollow body having an interior space for accommodating the circuit board 50 in a sealed condition. In the present embodiment, the trunk portion 34 has a tubular shape having such a cross-sectional shape that is formed by replacing the short sides of a rectangle with arcs.

The cable insertion portion 38 of the housing 30 receives the cable 80 in an inserted condition and maintains electrical connection between the second terminals 70 and the cable 80. In the present embodiment, the cable insertion portion 38 protrudes from an end portion of the housing 30 on a side opposite the external connector 32.

Figure 3:
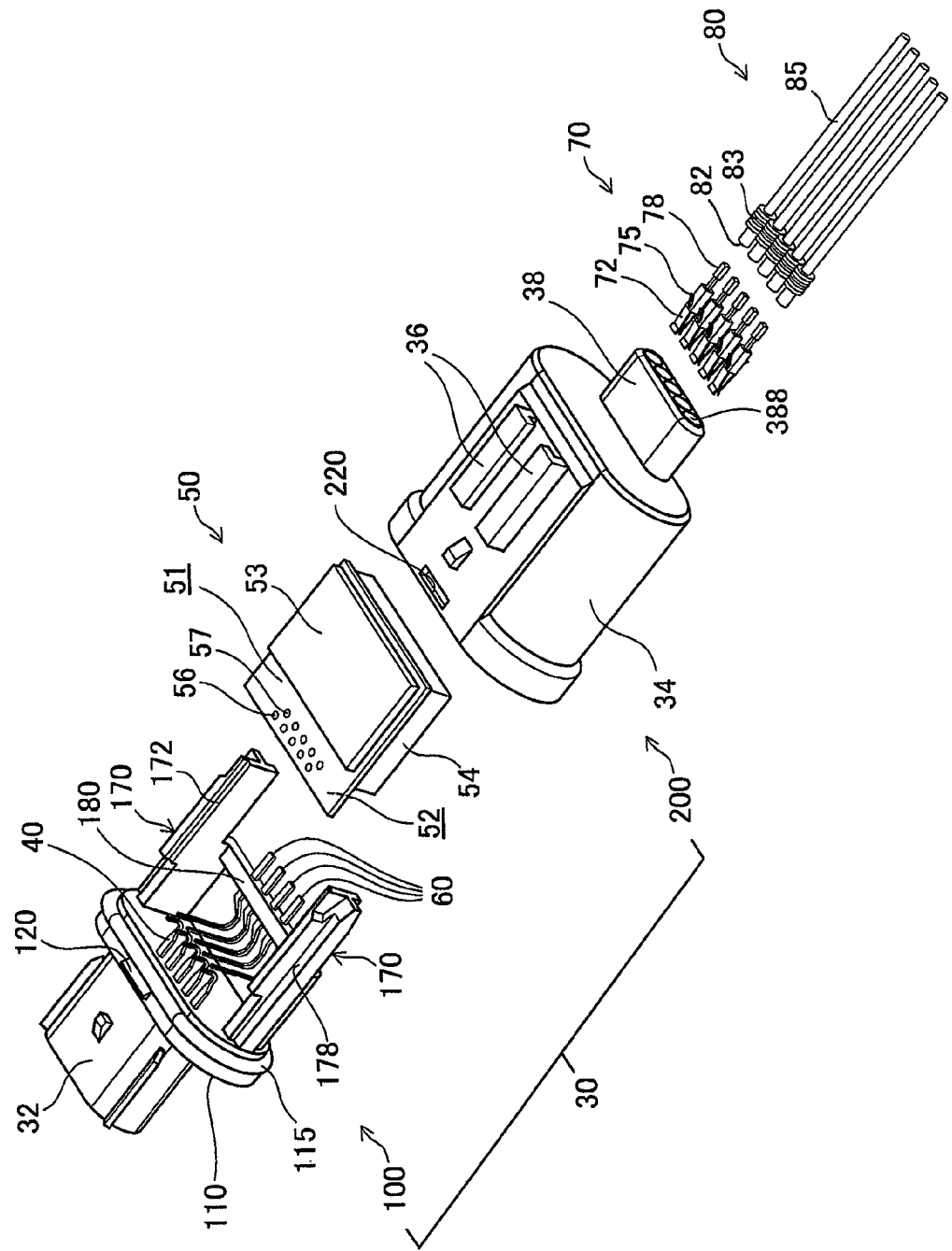
FIG. 3 Exploded perspective view showing the detailed configuration of the housing.
Figure 4:
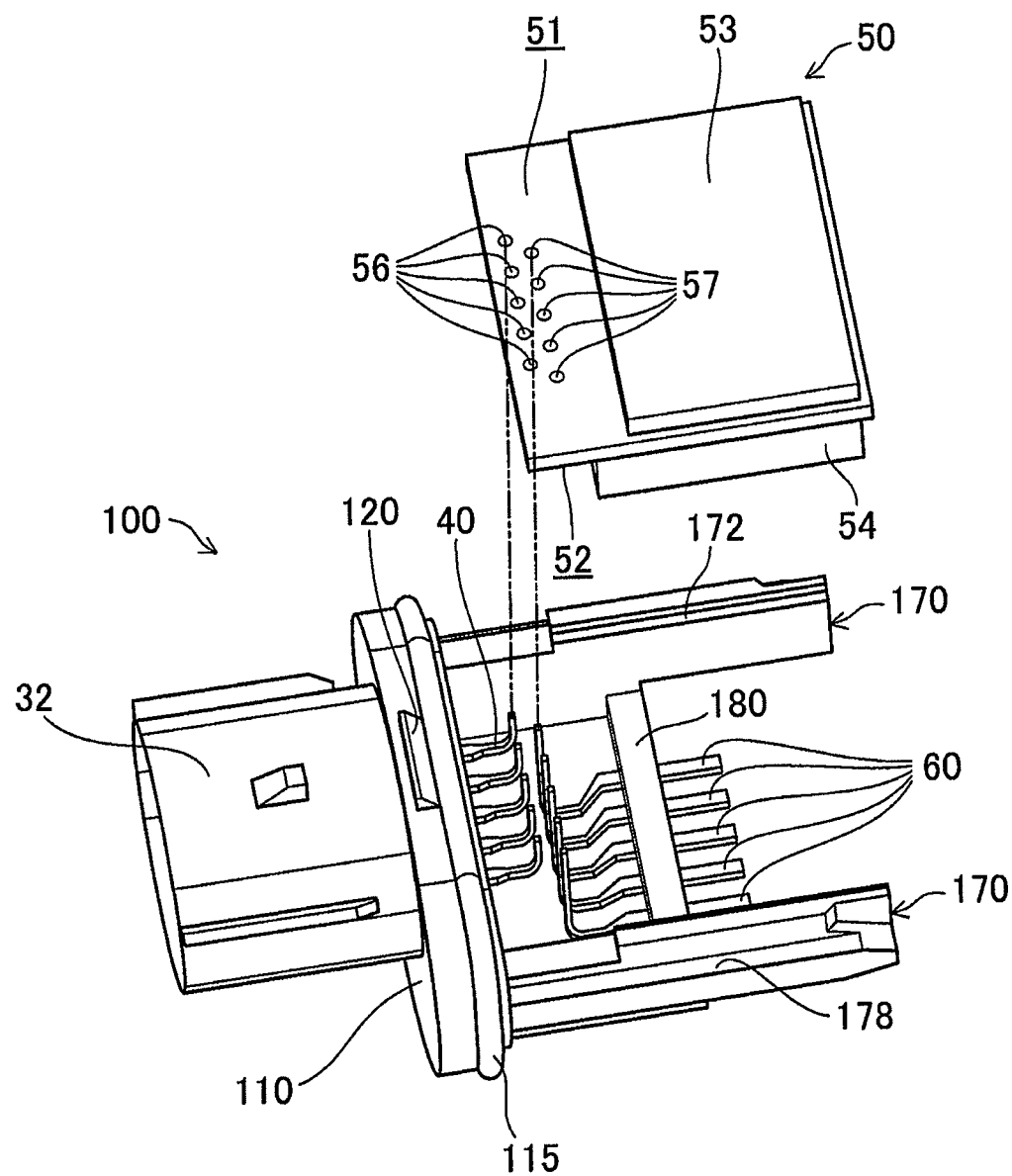
FIG. 4 Perspective view showing how a circuit board is mounted to a first member of the housing.
Figure 5:
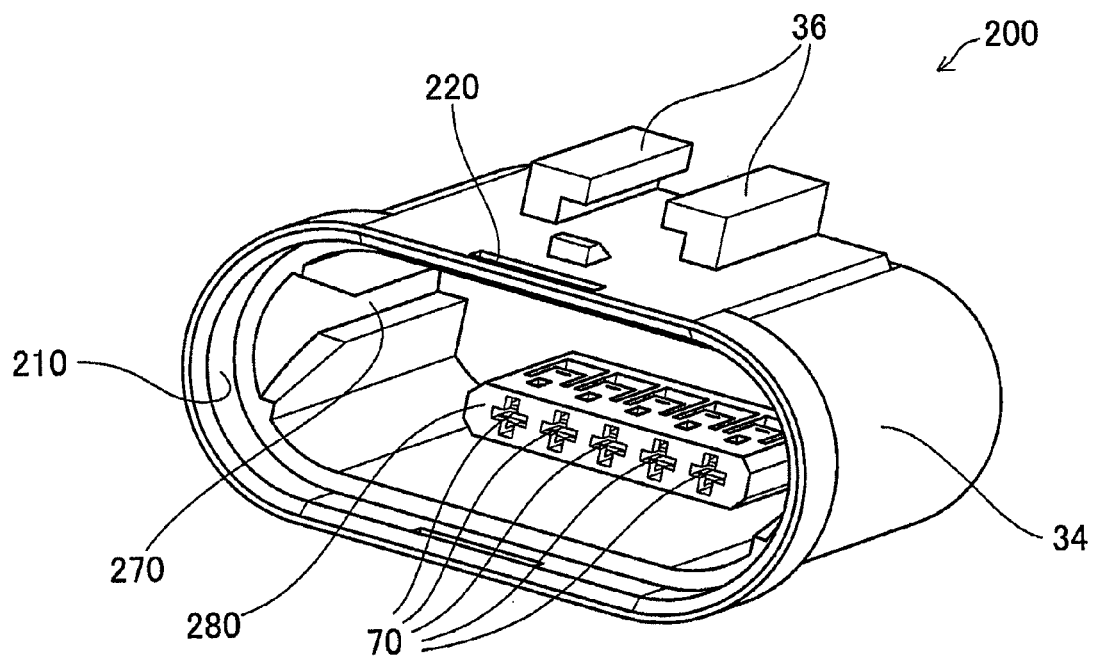
FIG. 5 Perspective view showing the inner configuration of a second member of the housing.
Figure 6:
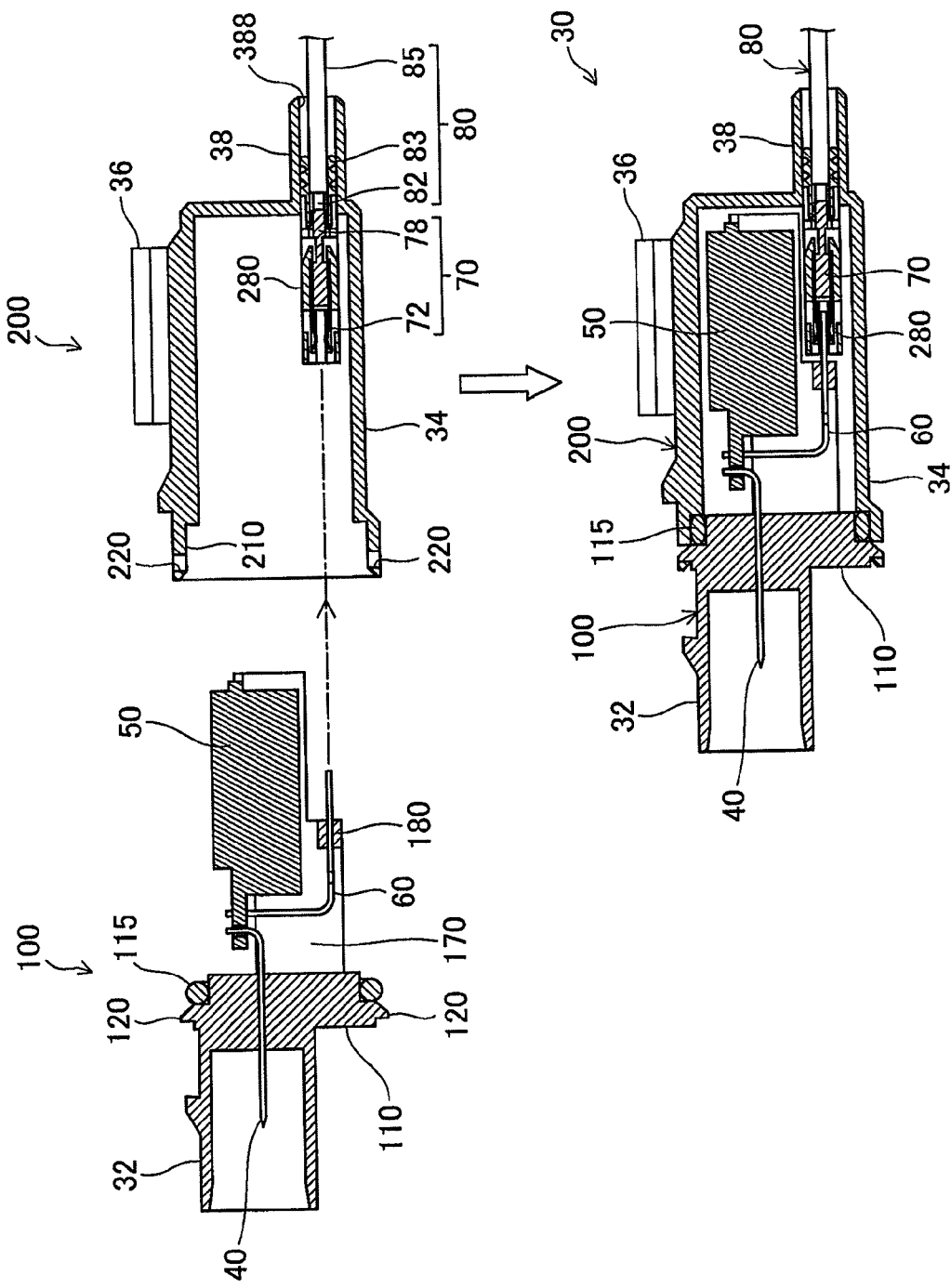
FIG. 6 Sectional view showing how the housing is assembled through engagement between the first member and the second member.

FIG. 3 is an exploded perspective view showing the detailed configuration of the housing 30. FIG. 4 is a perspective view showing how the circuit board 50 is mounted to a first member 100 of the housing 30. FIG. 5 is a perspective view showing the inner configuration of a second member 200 of the housing 30. FIG. 6 is a sectional view showing how the housing 30 is assembled through engagement between the first member 100 and the second member 200. FIG. 6 shows, at its upper side, how the cable 80 is attached to the second member 200 to which the second terminals 70 are attached and how the first member 100 to which the circuit board 50 is mounted is engaged with the second member 200. FIG. 6 shows, at its lower side, the assembled housing 30 in section.

As shown in FIG. 3 and at the lower side of FIG. 6, the housing 30 of the sensor apparatus 10 is composed of the first member 100 and the second member 200. The first member 100 is a lid body that functions as a lid of the second member 200 and includes the external connector 32. The second member 200 is a container body that functions as an opened container and includes the trunk portion 34, the engagement portion 36, and the cable insertion portion 38. The first member 100 has the external terminals 40 and the first terminals 60 provided in a mutually-spaced-apart condition and has the circuit board 50 mounted thereto. The second member 200 has the second terminals 70 provided therein and has the cable 80 attached thereto.

As shown in FIG. 6, the first member 100 of the housing 30 supports the circuit board 50 in a condition that the circuit board 50 is electrically connected to the external terminals 40. Also, the second member 200 of the housing 30 is engaged with the first member 100 to which the circuit board 50 is mounted, thereby accommodating the circuit board 50 in cooperation with the first member 100. The housing 30 has such a structure that, as a result of engagement between the first member 100 and the second member 200, the circuit board 50 is electrically connected to the cable 80. The structure of the housing 30 will be described in detail below.

As shown in FIGS. 3, 4, and 6, the first member 100 of the housing 30 includes a lid portion 110, locking ridges 120, two board support portions 170, and a terminal support portion 180. In the present embodiment, the first member 100 is formed of a resin having electric insulation, water resistance, and heat resistance.

The lid portion 110 of the first member 100 is formed into such a shape as to cover the opening of the second member 200, which is a container body. In the present embodiment, the lid portion 110 has such a shape that is formed by replacing the short sides of a rectangle with arcs, so as to coincide with the shape of the trunk portion 34 of the second member 200. In the present embodiment, an O-ring 115 is provided on the periphery of the lid portion 110 for sealing a gap between the lid portion 110 and the second member 200.

The lid portion 110 has the external connector 32 formed thereon and has the two board support portions 170 and the terminal support portion 180 formed on a side opposite the external connector 32. The external terminals 40 provided in the first member 100 are formed of an electrically conductive metal; extend through the lid portion 110 from a side toward the external connector 32 to a side toward the board support portions 170; and has end portions, on the side toward the board support portions 170, bent toward the circuit board 50. In the present embodiment, the external terminals 40 are integrally molded to the lid portion 110 of the first member 100. In the present embodiment, the number of the external terminals 40 is five. However, in other embodiments, the number of the external terminals 40 may be four or less, or six or greater in view of the configuration of the circuit board 50, the type of communication of electric signals with the control unit 90, etc.

The locking ridges 120 of the first member 100 are adapted to lock the second member 200 in position. In the present embodiment, the locking ridges 120 are formed on the periphery of the lid portion 110 and are located adjacent to the O-ring 115.

The two board support portions 170 of the first member 100 protrude from the lid portion 110 and support the circuit board 50 therebetween. The two board support portions 170 have respective recesses 172 formed on their inner sides and extending along the protruding direction of the board support portions 170. The recesses 172 receive the circuit board 50. In the present embodiment, the two board support portions 170 have respective guides 178 formed on their outer sides and extending along the protruding direction of the board support portions 170 for guiding the second member 200 to a position of engagement with the first member 100.

The terminal support portion 180 of the first member 100 is provided between the two board support portions 170 in a bridging condition and supports the first terminals 60. The first terminals 60 provided in the first member 100 are formed of an electrically conductive metal; extends through the terminal support portion 180 along the protruding direction of the board support portions 170; and has end portions, on a side toward the lid portion 110, bent toward the circuit board 50. In the present embodiment, the number of the first terminals 60 is five. However, in other embodiments, the number of the first terminals 60 may be four or less, or six or greater in view of the type and structure of the sensor 20, etc. In the present embodiment, the first terminals 60 are integrally molded to the terminal support portion 180 of the first member 100.

The circuit board 50 to be mounted to the first member 100 has two opposite surfaces; namely, a first board surface 51 and a second board surface 52. The first board surface 51 and the second board surface 52 have respective mounting sections 53 and 54 which are formed thereon and in which a plurality of circuit components are mounted. The circuit board 50 has terminal holes 56 and 57 extending therethrough between the first board surface 51 and the second board surface 52.

When the circuit board 50 is placed on the two board support portions 170 such that the second board surface 52 of the circuit board 50 is in contact with the recesses 172, the external terminals 40 provided in the first member 100 are inserted into the respective terminal holes 56 of the circuit board 50, and the first terminals 60 provided in the first member 100 are inserted into the respective terminal holes 57 of the circuit board 50. Subsequently, the circuit board 50 is soldered to the external terminals 40 and to the first terminals 60, whereby, as shown at the upper side of FIG. 6, the circuit board 50 is electrically connected to the external terminals 40 and to the first terminals 60. By this procedure, the first terminals 60 provided in the first member 100 function as terminals for allowing the sensor 20 to be electrically connected to the circuit board 50.

As shown in FIGS. 3, 5, and 6, the second member 200 of the housing 30 includes an opening portion 210, locking holes 220, guides 270, and a terminal holder 280. In the present embodiment, the second member 200 is formed of a resin having electric insulation, water resistance, and heat resistance.

The opening portion 210 of the second member 200 forms an opening of the second member 200, which is a container body, and is formed into such a shape as to be fitted to the lid portion 110 of the first member 100. In the present embodiment, the opening portion 210 has the locking holes 220 formed in the periphery thereof and adapted to be engaged with the corresponding locking ridges 120 of the first member 100.

As shown in FIG. 5, the guides 270 of the second member 200 are formed on the inner side of the second member 200, which is a container body, and assume the form of respective recesses to be fitted to the guides 178 of the two board support portions 170 of the first member 100.

As shown in FIGS. 5 and 6, the terminal holder 280 of the second member 200 is formed at the inside of the second member 200, which is a container body, and holds the second terminals 70. The terminal holder 280 is provided in such a manner as to correspond to the cable insertion portion 38 formed at the outside of the second member 200 and communicates with cable insertion holes 388 formed in the cable insertion portion 38 and adapted to receive insertion of the cable 80.

Each of insulated wires of the cable 80 attached to the second member 200 includes a core wire end portion 82, a seal member 83, and coating 85. The coating 85 of an insulated wire of the cable 80 is formed of an electrically insulative material and covers a core wire. The core wire end portion 82 of an insulated wire of the cable 80 is such an end portion of a core wire that is exposed from the coating 85. The seal member 83 of an insulated wire of the cable 80 is a tubular elastic member formed of synthetic rubber and is provided on the outer circumference of the coating 85 at a position located toward the core wire end portion 82. The seal member 83, together with the core wire end portion 82, is inserted into the corresponding cable insertion hole 388 of the cable insertion portion 38 and comes into close contact with the inner wall of the cable insertion hole 388, thereby providing a watertight seal between an insulated wire of the cable 80 and the second member 200 (the housing 30). In the present embodiment, the cable 80 is a bundle of five insulated wires in a covered condition. However, in other embodiments, the number of the insulated wires may be four or less, or six or greater in view of the type and structure of the sensor 20, etc.

The second terminals 70 attached to the second member 200 are formed of an electrically conductive metal. In the present embodiment, the number of the second terminals 70 is five. However, in other embodiments, the number of the second terminals 70 may be four or less, or six or greater. In the present embodiment, each of the second terminals 70 includes an engagement portion 72 engageable with the corresponding first terminal 60; locking ridges 75 to be locked into engagement with the terminal holder 280; and a crimp portion 78 which can be fixedly crimped to the core wire end portion 82 of a corresponding insulated wire of the cable 80. In attaching each of the second terminals 70 to the second member 200, in a condition in which the core wire end portion 82 of an insulated wire of the cable 80 is fixedly crimped to the crimp portion 78 of the second terminal 70, the second terminal 70, together with the insulated wire of the cable 80, is inserted, with the engagement portion 72 in the lead, into the terminal holder 280 through the corresponding cable insertion hole 388 of the cable insertion portion 38. As shown at the upper side of FIG. 6, the second terminals 70 inserted into the terminal holder 280 are fixed to the terminal holder 280 by means of the locking ridges 75, and the insulated wires of the cable 80 are fixed in the corresponding cable insertion holes 388 of the cable insertion portion 38.

As shown at the lower side of FIG. 6, as a result of engagement between the first member 100 and the second member 200 of the housing 30, the first terminals 60 of the first member 100 are engaged with the corresponding engagement portions 72 of the second terminals 70 of the second member 200. Thus, the first terminals 60 and the second terminals 70 are engaged with each other and electrically connected to each other. In the present embodiment, in a condition in which the first member 100 and the second member 200 of the housing 30 are engaged with each other, the first terminals 60 and the second terminals 70, together with the circuit board 50, are sealed in the housing 30. In the present embodiment, in a condition in which the first member 100 and the second member 200 of the housing 30 are engaged with each other, the first terminals 60 and the second terminals 70 are disposed along the second board surface 52 of the circuit board 50.

A-2. Effects

According to the above-described sensor apparatus 10, the first member 100 and the second member 200 are engaged with each other, thereby accommodating the circuit board 50 in the housing 30 and at the same time establishing an electric connection of the cable 80 to the circuit board 50. As a result, workability in a process of manufacturing the sensor apparatus 10 can be improved. Also, prior to engagement between the first member 100 and the second member 200, by means of inspection of the condition in which the circuit board 50 is mounted to the first member 100 as well as inspection of the condition in which the cable 80 is attached to the second member 200, productivity in manufacturing products; i.e., the sensor apparatus 10, can be improved. Particularly, prior to engagement between the first member 100 and the second member 200, by means of the cable 80 connected to the sensor 20 being attached to the second member 200, electrical characteristics of the sensor 20 can be inspected by use of an inspection device connected to the second terminals 70 held in the terminal holder 280. By this procedure, before engagement with the first member 100, the sensor 20 can be inspected for any abnormality (abnormality in wiring, element cracking, etc.). When any abnormality is found in the sensor 20, what is required is just to replace the abnormal sensor 20 with a normal one. In view of this, also, productivity in manufacturing the sensor apparatus 10 can be improved.

Also, as a result of engagement between the first member 100 and the second member 200, the first terminals 60 provided in the first member 100 and the second terminals 70 provided in the second member 200 are engaged with each other and electrically connected to each other; thus, the housing 30 can avoid having a complex structure.

Also, in a condition that the first member 100 and the second member 200 are engaged with each other, the first terminals 60 provided in the first member 100 and the second terminals 70 provided in the second member 200, together with the circuit board 50, are sealed in the housing 30. Thus, similar to the circuit board 50, the first terminals 60 and the second terminals 70 can be protected.

Also, in a condition that the first member 100 and the second member 200 are engaged with each other, the first terminals 60 provided in the first member 100 and the second terminals 70 provided in the second member 200 are disposed along the second board surface 52 of the circuit board 50. Thus, the size of the housing 30 can be reduced.

Also, the external terminals 40 and the first terminals 60 provided in the first member 100 are integrally molded to the first member 100. Thus, a work step of individually attaching the external terminals 40 and the first terminals 60 to the first member 100 can be eliminated.

Also, the first member 100 further includes the two board support portions 170, which support the circuit board 50, and the terminal support portion 180, which supports the first terminals 60. Thus, while sufficient mounting rigidity is ensured in mounting the circuit board 50 and the first terminals 60 to the first member 100, the size of the housing 30 can be reduced.

Also, the two board support portions 170 have the respective guides 178 for guiding the second member 200 to a position of engagement with the first member 100. Thus, workability can be improved in engaging the first member 100 and the second member 200 with each other.

Also, the second member 200 is a container body that functions as an opened container, and the first member 100 is a lid body that functions as a lid of the second member 200. Thus, workability can be improved in mounting the circuit board 50 to the first member 100 without impairment in protection of the circuit board 50 by the housing 30.

B. Second Embodiment

B-1. Configuration of Sensor Apparatus

The general configuration of the sensor apparatus 10 according to a second embodiment of the present invention is similar to that of the first embodiment shown in FIG. 1. Similar to the first embodiment, the sensor apparatus 10 of the second embodiment includes the sensor 20, the housing 30, the external terminals 40, the circuit board 50, the first terminals 60, the second terminals 70, and the cable 80. In the description of the second embodiment, structural components of the sensor apparatus 10 of the second embodiment similar in function to those of the first embodiment are denoted by the same reference numerals as those of the first embodiment.

Figure 7:
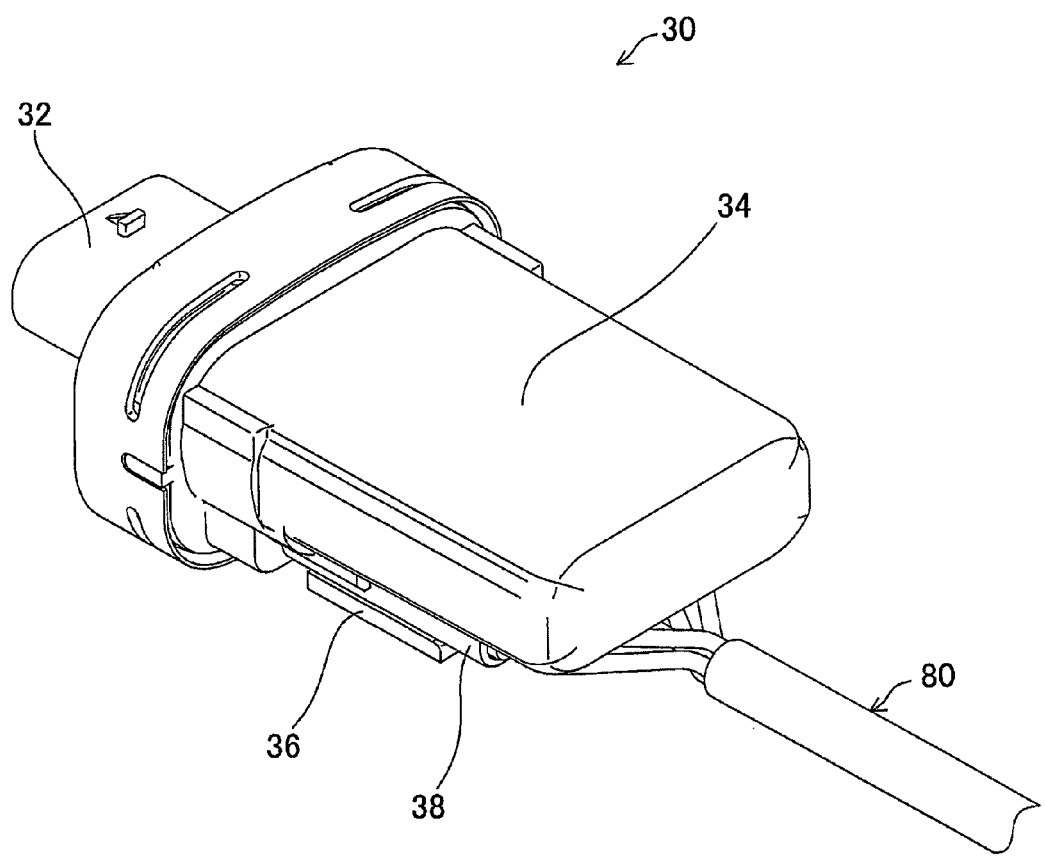
FIG. 7 Perspective view showing the detailed configuration of the housing in a second embodiment of the present invention.
Figure 8:
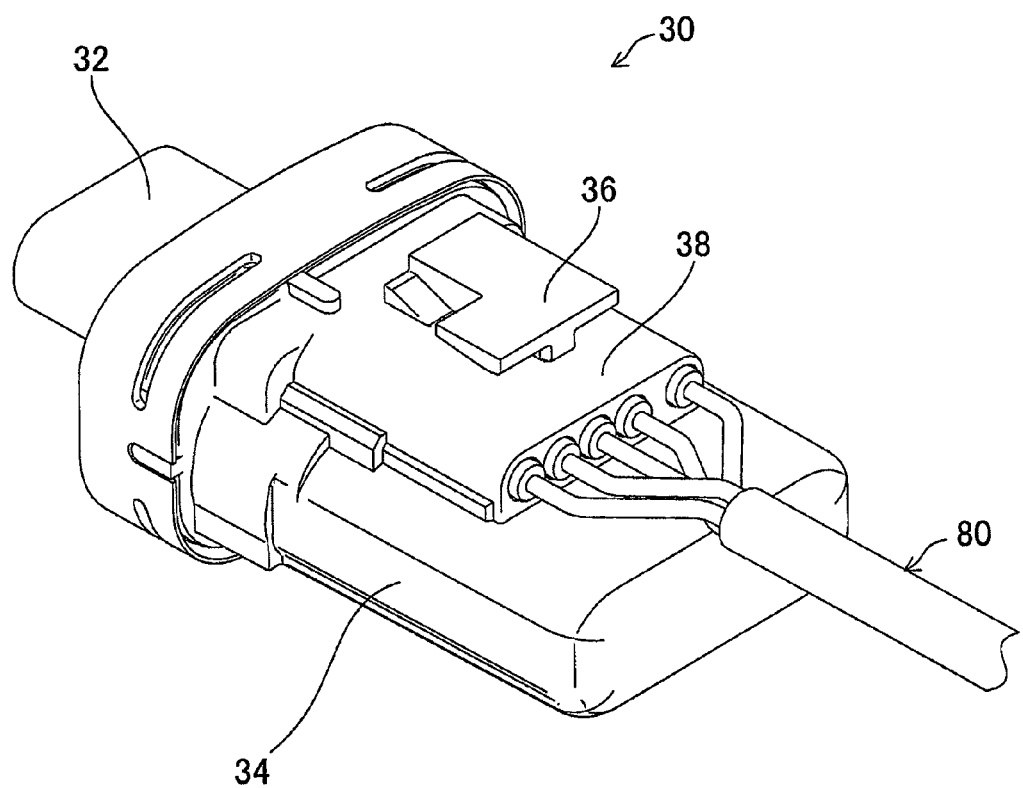
FIG. 8 Perspective view showing the detailed configuration of the housing in the second embodiment.

FIGS. 7 and 8 are perspective views showing the detailed configuration of the housing 30 in the second embodiment. FIG. 7 is a perspective view of the housing 30 as viewed from the upper side of the housing 30, and FIG. 8 is a perspective view of the housing 30 as viewed from the back side of the housing 30. The housing 30 of the sensor apparatus 10 includes the external connector 32, the trunk portion 34, the engagement portion 36, and the cable insertion portion 38.

The external connector 32 of the housing 30 allows the control unit 90 to be electrically connected to the circuit board 50. Through engagement with a connector (not shown) associated with the control unit 90, the external connector 32 maintains electrical connection to the control unit 90 through the external terminals 40. In the present embodiment, the external connector 32 is provided in a protruding condition at the end of the trunk portion 34 and surrounds the external terminals 40 protruding from the trunk portion 34.

The trunk portion 34 of the housing 30 is a hollow body having an interior space for accommodating the circuit board 50 in a sealed condition. In the present embodiment, the trunk portion 34 has a tubular shape having such a cross-sectional shape that is formed by replacing the short sides of a rectangle with arcs.

The engagement portion 36 of the housing 30 is engageable with another member (not shown). The housing 30 can be fixed in position by use of the engagement portion 36. In the present embodiment, the engagement portion 36 is provided on the back side of the trunk portion 34 via the cable insertion portion 38.

The cable insertion portion 38 of the housing 30 receives the cable 80 in an inserted condition and Maintains electrical connection between the second terminals 70 and the cable 80. In the present embodiment, the cable insertion portion 38 is provided on the back side of the trunk portion 34. In the present embodiment, the cable 80 is inserted into the cable insertion portion 38 from a side opposite the external connector 32.

Figure 9:
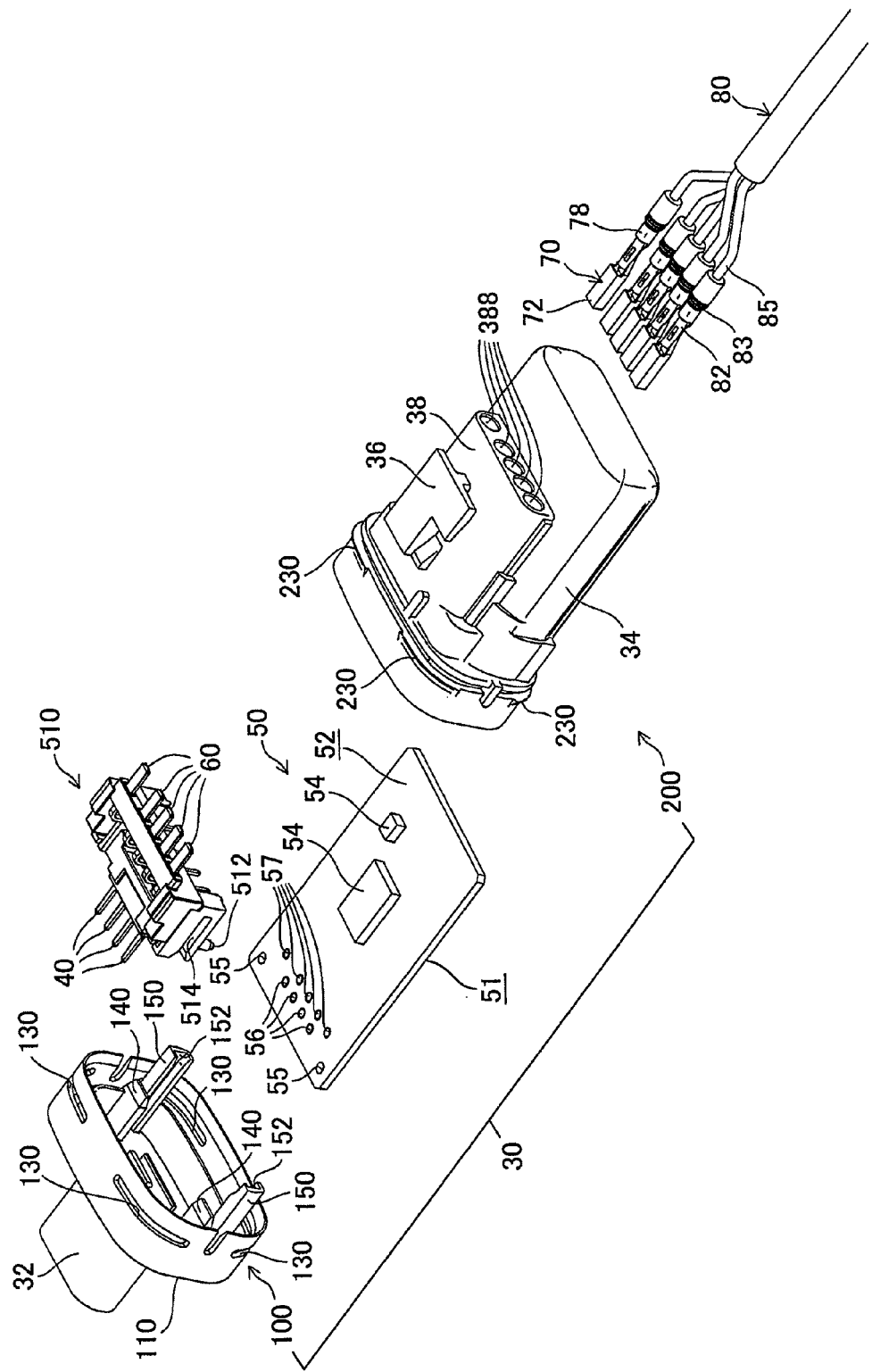
FIG. 9 Exploded perspective view showing the detailed configuration of the housing in the second embodiment.

FIG. 9 is an exploded perspective view showing the detailed configuration of the housing 30 in the second embodiment. As shown in FIG. 9, the housing 30 of the sensor apparatus 10 is an assembly of the first member 100 and the second member 200.

The first member 100 of the housing 30 is a lid body that functions as a lid of the second member 200. The first member 100 includes the external connector 32.

In the second embodiment, the circuit board 50, together with a terminal block 510, is mounted to the first member 100. The terminal block 510 holds the external terminals 40 and the first terminals 60 provided in a mutually-spaced-apart condition. In the second embodiment, the terminal block 510 is fixed to the circuit board 50 by means of the external terminals 40 and the first terminals 60 being soldered to the circuit board 50. In the second embodiment, the external terminals 40 and the first terminals 60 are provided in the first member 100 by means of the terminal block 510 being locked into engagement with the first member 100. The first terminals 60 provided in the first member 100 function as terminals for allowing the sensor 20 to be electrically connected to the circuit board 50.

The second member 200 of the housing 30 is a container body that functions as an opened container. The second member 200 has the trunk portion 34, the engagement portion 36, and the cable insertion portion 38. The second terminals 70 and the cable 80 are attached to the second member 200.

Figure 10:
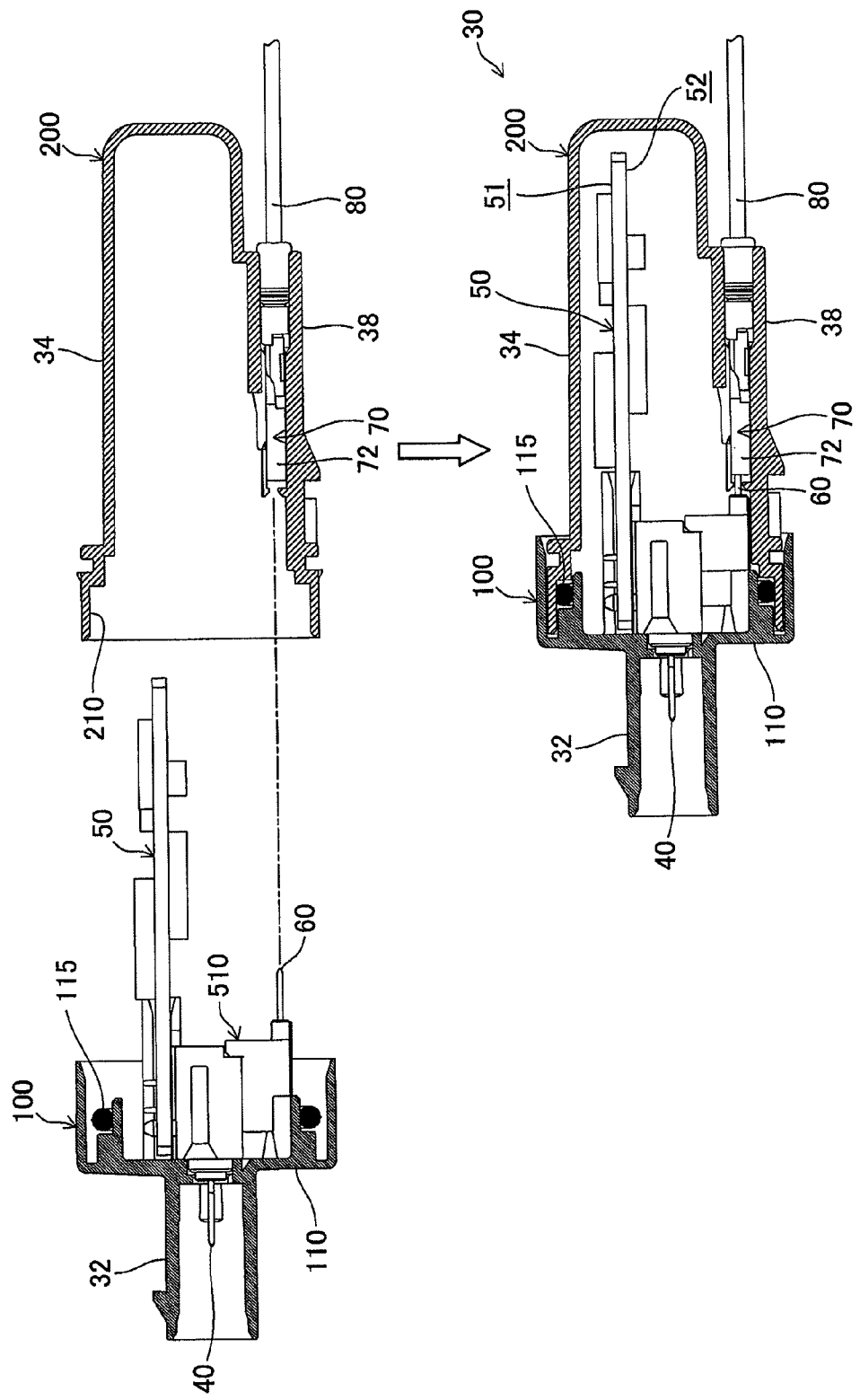
FIG. 10 Sectional view showing how the housing is assembled through engagement between the first member and the second member in the second embodiment.

FIG. 10 is a sectional view showing how the housing 30 is assembled through engagement between the first member 100 and the second member 200 in the second embodiment. FIG. 10 shows, at its upper side, how the first member 100 to which the circuit board 50 is mounted is engaged with the second member 200 to which the second terminals 70 and the cable 80 are attached. FIG. 10 shows, at its the lower side, the assembled housing 30 in section.

As shown in FIG. 10, the first member 100 of the housing 30 supports the circuit board 50 in a condition that the circuit board 50 is soldered to the external terminals 40 and to the first terminals 60. Also, the second member 200 of the housing 30 is engaged with the first member 100 to which the circuit board 50 is mounted, thereby accommodating the circuit board 50 in cooperation with the first member 100. The housing 30 has such a structure that, as a result of engagement between the first member 100 and the second member 200, the circuit board 50 is electrically connected to the cable 80. The structure of the housing 30 will be described in detail below.

Figure 11:
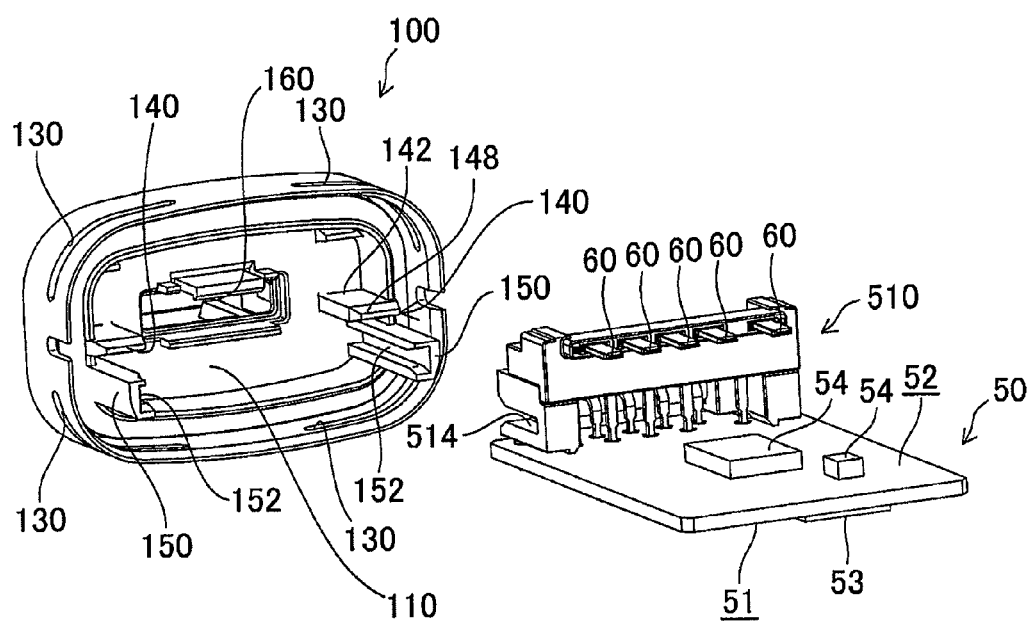
FIG. 11 Explanatory view showing how the circuit board is mounted to the first member.

FIG. 11 is an explanatory view showing how the circuit board 50 is mounted to the first member 100. The first member 100 of the housing 30 has the lid portion 110, locking holes 130, two protrusions 140, two board guide portions 150, and a terminal block locking portion 160. In the present embodiment, the first member 100 is formed of a resin having electric insulation, water resistance, and heat resistance.

The lid portion 110 of the first member 100 is formed into such a shape as to cover the opening of the second member 200, which is a container body. In the present embodiment, the lid portion 110 has such a shape that is formed by replacing the short sides of a rectangle with arcs, so as to coincide with the shape of the trunk portion 34 of the second member 200. In the present embodiment, as shown in FIG. 10, the lid portion 110 has the external connector 32 formed at the outside of the lid portion 110, and the O-ring 115 is provided on a side opposite the external connector 32; i.e., at the inside of the lid portion 110, for sealing a gap between the lid portion 110 and the second member 200.

The locking holes 130 of the first member 100 are through holes for locking the second member 200 in position. In the present embodiment, the first member 100 has four locking holes 130 formed at four corresponding corners of the lid portion 110.

The two protrusions 140 of the first member 100 are provided in a protruding condition at the inside of the lid portion 110. The terminal block 510 is held between the two protrusions 140. Each of the two protrusions 140 has a proximal end portion 142 and a distal end portion 148. The proximal end portions 142 of the protrusions 140 are fixed to the lid portion 110. The protrusions 140 extend from the proximal end portions 142 to the distal end portions 148 in a direction of engaging the first member 100 with the second member 200. In the present embodiment, spacing between the two protrusions 140 is narrower on a side toward the proximal end portions 142 than on a side toward the distal end portions 148. By virtue of this spacing feature, while attachment of the terminal block 510 to the first member 100 is facilitated, accuracy can be improved in positioning the external terminal 40 relative to the first member 100.

The two board guide portions 150 of the first member 100 are provided in a protruding condition at the inside of the lid portion 110 and are adapted to guide the circuit board 50 therebetween (the circuit board 50 is loosely fitted between the two board guide portions 150). The two board guide portions 150 have respective grooves 152 formed at the inside thereof along the protruding direction thereof for allowing the circuit board 50 to rest in the grooves 152. The circuit board 50 is mounted between the two board guide portions 150 as follows. In a condition in which the terminal block 510 is fixed to the circuit board 50, while the terminal block 510 is fitted between the two protrusions 140, the circuit board 50 is loosely fitted between the two board guide portions 150. By this procedure, the circuit board 50 can be mounted to the first member 100 without hindering the positioning of the external terminals 40 relative to the first member 100.

The terminal block locking portion 160 of the first member 100 is provided in a protruding condition at the inside of the lid portion 110 and is adapted to lock the terminal block 510 in position. The terminal block locking portion 160 locks the terminal block 510 in position, thereby preventing the terminal block 510 held between the two protrusions 140 from coming out from between the two protrusions 140.

As shown in FIGS. 9 and 11, the circuit board 50 to be mounted to the first member 100 has two opposite surfaces; namely, the first board surface 51 and the second board surface 52. The first board surface 51 and the second board surface 52 of the circuit board 50 have respective mounting sections 53 and 54 which are formed thereon and in which a plurality of circuit components are mounted. The circuit board 50 has through holes 55 and the terminal holes 56 and 57 formed therein.

The through holes 55 of the circuit board 50 extend through the circuit board 50 between the first board surface 51 and the second board surface 52 and are engaged with the terminal block 510. Through engagement of the through holes 55 with the terminal block 510, the terminal block 510 is positioned relative to the circuit board 50. In the present embodiment, the circuit board 50 has two through holes 55.

The terminal holes 56 of the circuit board 50 extend through the circuit board 50 between the first board surface 51 and the second board surface 52. One ends of the external terminals 40 held in the terminal block 510 are inserted into the respective terminal holes 56, followed by soldering. By this procedure, the circuit board 50 is electrically connected to the external terminals 40. In the present embodiment, the circuit board 50 has four terminal holes 56 so as to correspond in quantity to the external terminals 40.

The terminal holes 57 of the circuit board 50 extend through the circuit board 50 between the first board surface 51 and the second board surface 52. One ends of the first terminals 60 held in the terminal block 510 are inserted into the respective terminal holes 57, followed by soldering. By this procedure, the circuit board 50 is electrically connected to the first terminals 60. In the present embodiment, the circuit board 50 has five terminal holes 57 so as to correspond in quantity to the first terminals 60.

Figure 12:
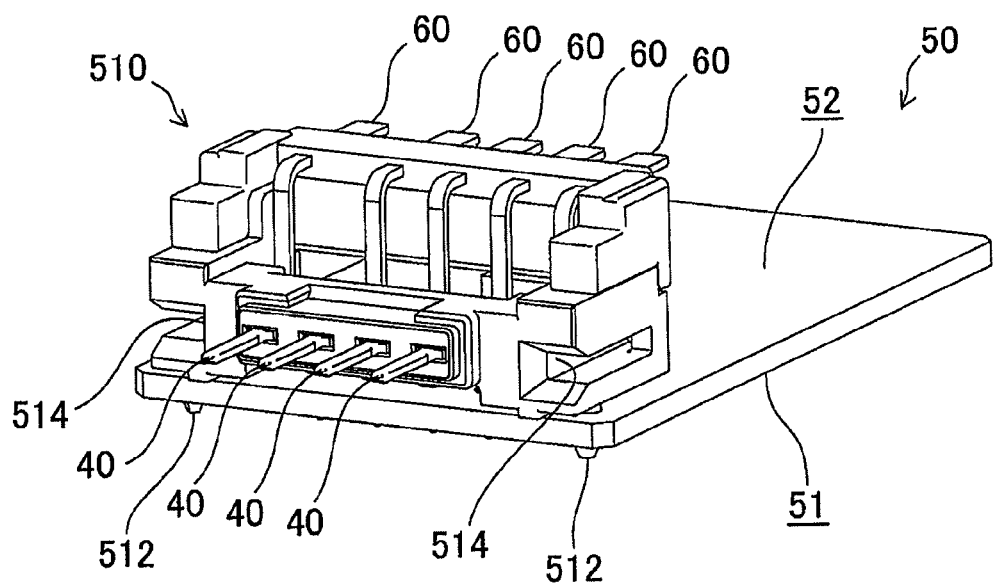
FIG. 12 Perspective view showing a terminal block fixed to the circuit board.
Figure 13:
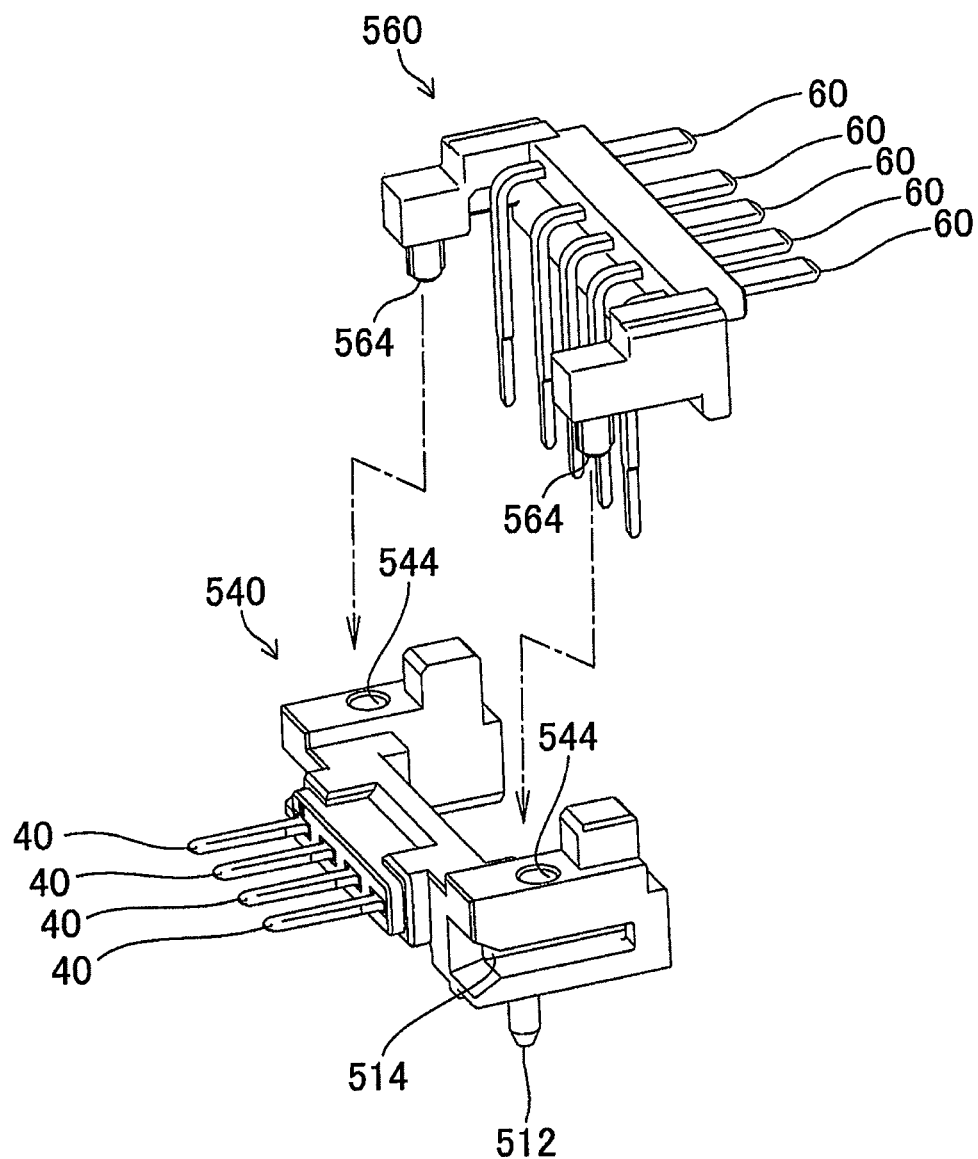
FIG. 13 Exploded perspective view showing the detailed configuration of the terminal block.

FIG. 12 is a perspective view showing the terminal block 510 fixed to the circuit board 50. FIG. 13 is an exploded perspective view showing the detailed configuration of the terminal block 510. As shown in FIG. 13, the terminal block 510 is an assembly of an external-terminal-side terminal block 540 and a first-terminal-side terminal block 560.

The external-terminal-side terminal block 540 and the first-terminal-side terminal block 560 are separate members. The external-terminal-side terminal block 540 holds the external terminals 40, and the first-terminal-side terminal block 560 holds the first terminals 60. Thus, when the specifications (material, plating, shape, quantity, etc.) of either of the external terminals 40 and the first terminals 60 are to be changed, such a change can be made through replacement of either the external-terminal-side terminal block 540 or the first-terminal-side terminal block 560.

Figure 14:
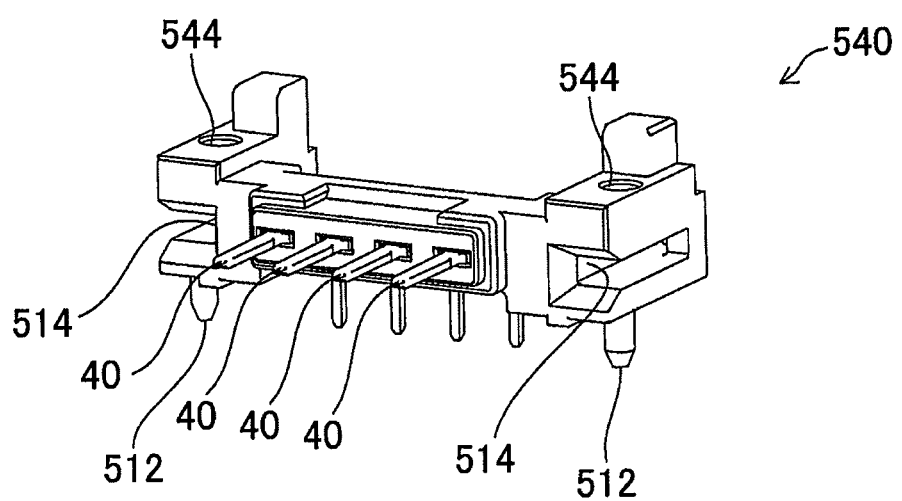
FIG. 14 Perspective view showing an external-terminal-side terminal block.

FIG. 14 is a perspective view showing the external-terminal-side terminal block 540. The external-terminal-side terminal block 540 holds the external terminals 40 and includes two protrusions 512, two grooves 514, and two engagement holes 544. The two protrusions 512 of the external-terminal-side terminal block 540 are fitted into the two through holes 55, respectively, of the circuit board 50. The two grooves 514 of the external-terminal-side terminal block 540 are fitted to the two protrusions 140, respectively, of the first member 100. The two engagement holes 544 of the external-terminal-side terminal block 540 are engaged with the first-terminal-side terminal block 560 for positioning. In the present embodiment, the external-terminal-side terminal block 540 is molded integrally with the external terminals 40 by use of a resin having electric insulation, water resistance, and heat resistance.

The external terminals 40 provided in the external-terminal-side terminal block 540 are formed of an electrically conductive metal. In the present embodiment, the external terminals 40 are bent into a shape resembling the letter L. In the present embodiment, the external-terminal-side terminal block 540 has four external terminals 40. However, in other embodiments, the number of the external terminals 40 may be three or less, or five or greater in view of the configuration of the circuit board 50, the type of communication of electric signals with the control unit 90, etc.

Figure 15:
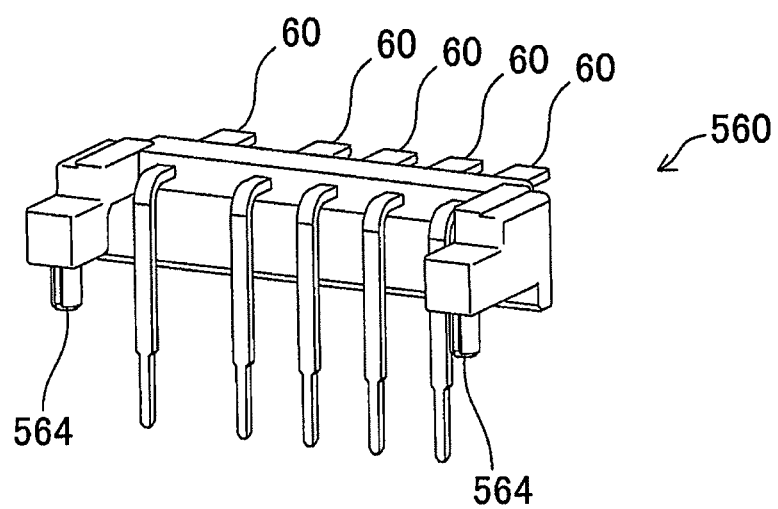
FIG. 15 Perspective view showing a first-terminal-side terminal block.

FIG. 15 is a perspective view showing the first-terminal-side terminal block 560. The first-terminal-side terminal block 560 holds the first terminals 60 and includes two engagement protrusions 564 to be fitted into the two engagement holes 544, respectively, of the external-terminal-side terminal block 540. In the present embodiment, the first-terminal-side terminal block 560 is molded integrally with the first terminals 60 by use of a resin having electric insulation, water resistance, and heat resistance.

The first terminals 60 provided in the first-terminal-side terminal block 560 are formed of an electrically conductive metal. In the present embodiment, the first terminals 60 are bent into a shape resembling the letter L. In the present embodiment, the first-terminal-side terminal block 560 has five first terminals 60. However, in other embodiments, the number of the first terminals 60 may be four or less, or six or greater in view of the configuration of the circuit board 50, the type of communication of electric signals with the control unit 90, etc.

Figure 16:
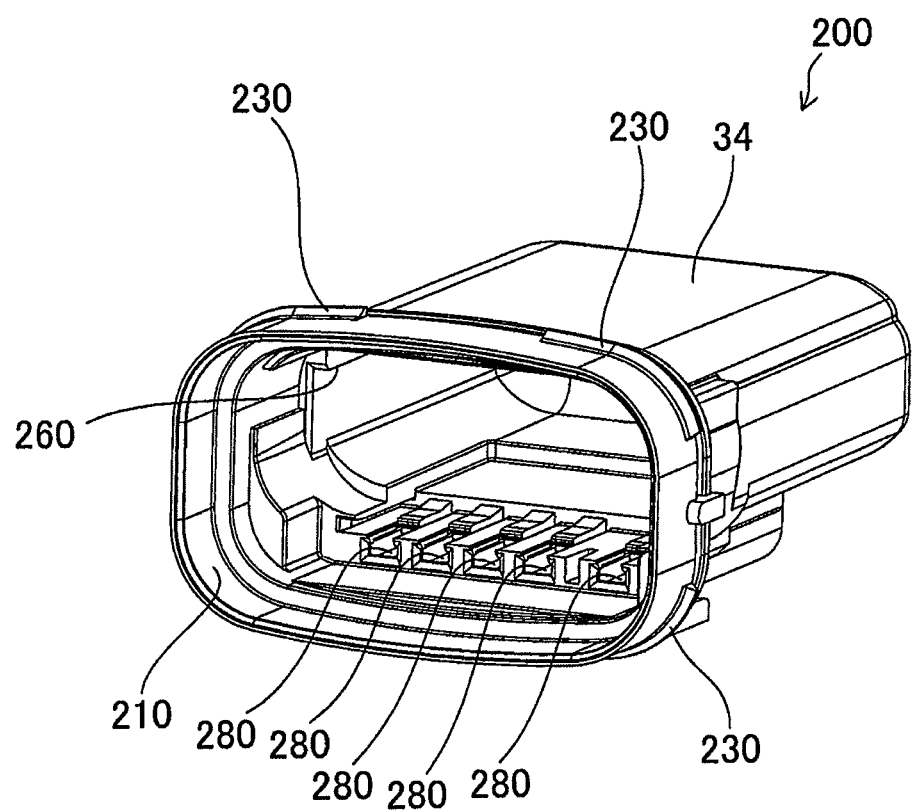
FIG. 16 Perspective view showing the detailed configuration of the second member in the second embodiment.
Figure 17:
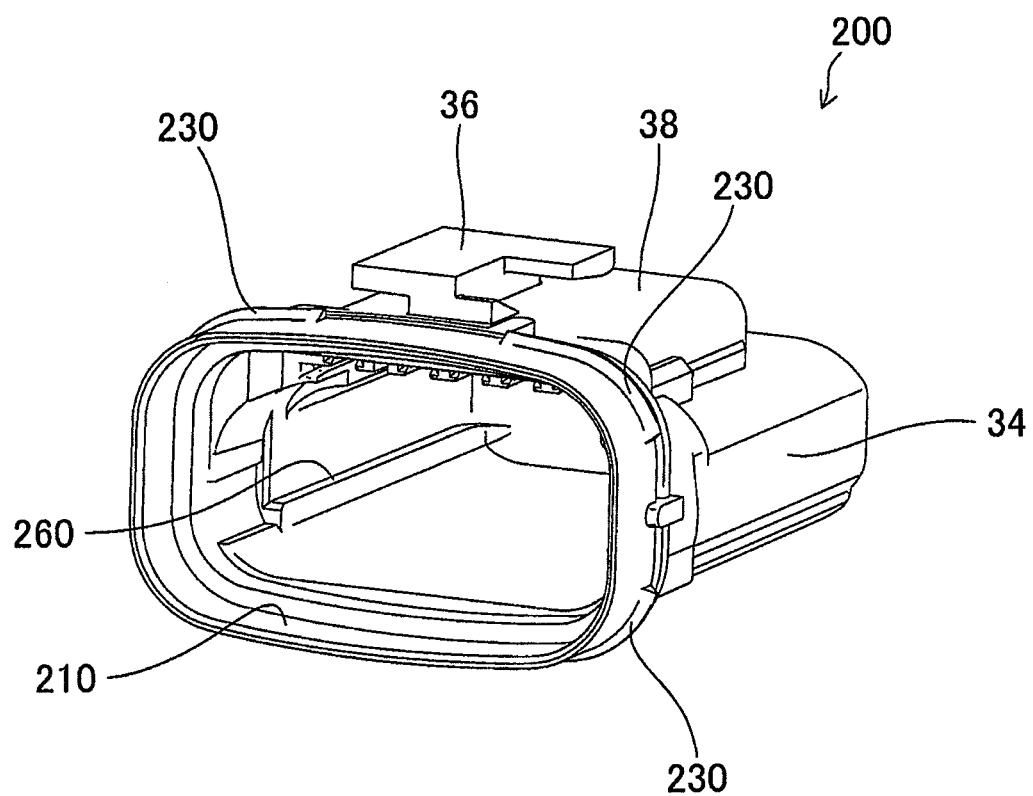
FIG. 17 Perspective view showing the detailed configuration of the second member in the second embodiment.

FIGS. 16 and 17 are perspective views showing the detailed configuration of the second member 200 in the second embodiment. FIG. 16 is a perspective view of the second member 200 as viewed from the upper side of the second member 200. FIG. 17 is a perspective view of the second member 200 as viewed from the back side of the second member 200. The second member 200 of the housing 30 includes the opening portion 210, locking ridges 230, guides 260, and terminal holders 280. In the present embodiment, the second member 200 is integrally molded from a resin having electric insulation, water resistance, and heat resistance.

The opening portion 210 of the second member 200 forms an opening of the second member 200, which is a container body, and is formed into such a shape as to be fitted to the lid portion 110 of the first member 100.

The locking ridges 230 of the second member 200 lock the first member 100 in position. In the present embodiment, the second member 200 has four locking ridges 230 formed at the periphery of the opening portion 210 so as to correspond to the four locking holes 130 of the first member 100.

The guides 260 of the second member 200 are formed at the inside of the second member 200, which is a container body. When the first member 100 and the second member 200 are to be engaged with each other, the guides 260 guide the circuit board 50 into the interior of the second member 200.

The terminal holders 280 of the second member 200 are formed at the inside of the second member 200, which is a container body, and are adapted to hold the respective second terminals 70. The terminal holders 280 are provided in such a manner as to correspond to the cable insertion portion 38 formed at the outside of the second member 200 and communicate with the cable insertion holes 388 formed in the cable insertion portion 38 and adapted to receive insertion of the cable 80 (see FIG. 9).

As shown in FIG. 9, each of insulated wires of the cable 80 attached to the second member 200 includes the core wire end portion 82, the seal member 83, and the coating 85. The coating 85 of an insulated wire of the cable 80 is formed of an electrically insulative material and covers a core wire. The core wire end portion 82 of an insulated wire of the cable 80 is such an end portion of a core wire that is exposed from the coating 85. The seal member 83 of an insulated wire of the cable 80 is a tubular elastic member formed of synthetic rubber and is provided on the outer circumference of the coating 85 at a position located toward the core wire end portion 82. The seal member 83, together with the core wire end portion 82, is inserted into the corresponding cable insertion hole 388 of the cable insertion portion 38 and comes into close contact with the inner wall of the cable insertion hole 388, thereby providing a watertight seal between an insulated wire of the cable 80 and the second member 200 (the housing 30). In the present embodiment, the cable 80 is a bundle of five insulated wires in a covered condition. However, in other embodiments, the number of the insulated wires of the cable 80 may be four or less, or six or greater in view of the type and structure of the sensor 20, etc.

The second terminals 70 attached to the second member 200 are formed of an electrically conductive metal. In the present embodiment, five second terminals 70 are attached to the second member 200. However, in other embodiments, the number of the second terminals 70 may be four or less, or six or greater. In the present embodiment, each of the second terminals 70 includes the engagement portion 72 engageable with the corresponding first terminal 60, and the crimp portion 78 which can be fixedly crimped to the core wire end portion 82 of a corresponding insulated wire of the cable 80. In attaching each of the second terminals 70 to the second member 200, in a condition in which the core wire end portion 82 of an insulated wire of the cable 80 is fixedly crimped to the crimp portion 78 of the second terminal 70, the second terminal 70, together with the insulated wire of the cable 80, is inserted, with the engagement portion 72 in the lead, into the corresponding terminal holder 280 through the corresponding cable insertion hole 388 of the cable insertion portion 38. By this procedure, the second terminals 70 are fixed to the corresponding terminal holders 280, and the insulated wires of the cable 80 are fixed in the corresponding cable insertion holes 388 of the cable insertion portion 38.

As shown at the lower side of FIG. 10, as a result of engagement between the first member 100 and the second member 200 of the housing 30, the first terminals 60 of the first member 100 are engaged with the corresponding engagement portions 72 of the second terminals 70 of the second member 200. Thus, the first terminals 60 and the second terminals 70 are engaged with each other and electrically connected to each other. In the present embodiment, in a condition in which the first member 100 and the second member 200 of the housing 30 are engaged with each other, the first terminals 60 and the second terminals 70, together with the circuit board 50, are sealed in the housing 30. In the present embodiment, in a condition in which the first member 100 and the second member 200 of the housing 30 are engaged with each other, the first terminals 60 and the second terminals 70 are disposed along the second board surface 52 of the circuit board 50.

B-2. Effects

According to the above-described sensor apparatus 10 of the second embodiment, the first member 100 and the second member 200 are engaged with each other, thereby accommodating the circuit board 50 in the housing 30 and at the same time establishing an electric connection of the cable 80 to the circuit board 50. As a result, workability in a process of manufacturing the sensor apparatus 10 can be improved. Also, prior to engagement between the first member 100 and the second member 200, by means of inspection of the condition in which the circuit board 50 is mounted to the first member 100 as well as inspection of the condition in which the cable 80 is attached to the second member 200, productivity in manufacturing products; i.e., the sensor apparatus 10, can be improved. Particularly, prior to engagement between the first member 100 and the second member 200, by means of the cable 80 connected to the sensor 20 being attached to the second member 200, electrical characteristics of the sensor 20 can be inspected by use of an inspection device connected to the second terminals 70 held in the respective terminal holders 280. By this procedure, before engagement with the first member 100, the sensor 20 can be inspected for any abnormality. When any abnormality is found in the sensor 20, what is required is just to replace the abnormal sensor 20 with a normal one. In view of this, also, productivity in manufacturing the sensor apparatus 10 can be improved.

Also, the terminal block 510 which holds the external terminals 40 and the first terminals 60 is locked into engagement with (mounted beforehand to) the first member 100, whereby the external terminals 40 and the first terminals 60 are provided in the first member 100. Thus, as compared with the case where the external terminals 40 and the first terminals 60 are integrally molded to the first member 100, workability in manufacture of the sensor apparatus 10 can be improved. For example, when the specifications (material, plating, shape, quantity, etc.) of the external terminals 40 and the first terminals 60 are to be changed, such a change can be made through replacement of the terminal block 510 rather than through replacement of the entire first member 100. Also, when moisture-proof coating is to be applied to the external terminals 40 and the first terminals 60 together with the circuit board 50, moisture-proof coating can be applied in a condition that these members are separated from the first member 100. Also, when the external terminals 40 and the first terminals 60 are to be soldered to the circuit board 50, soldering can be performed in a condition that these members are separated from the first member 100.

Also, as a result of engagement between the first member 100 and the second member 200, the first terminals 60 provided in the first member 100 and the second terminals 70 provided in the second member 200 are engaged with each other and electrically connected to each other; thus, the housing 30 can avoid having a complex structure.

Also, in a condition that the first member 100 and the second member 200 are engaged with each other, the first terminals 60 provided in the first member 100 and the second terminals 70 provided in the second member 200, together with the circuit board 50, are sealed in the housing 30. Thus, similar to the circuit board 50, the first terminals 60 and the second terminals 70 can be protected.

Also, in a condition that the first member 100 and the second member 200 are engaged with each other, the first terminals 60 provided in the first member 100 and the second terminals 70 provided in the second member 200 are disposed along the second board surface 52 of the circuit board 50. Thus, the size of the housing 30 can be reduced.

Also, the second member 200 is a container body that functions as an opened container, and the first member 100 is a lid body that functions as a lid of the second member 200. Thus, workability can be improved in mounting the circuit board 50 to the first member 100 without impairment in protection of the circuit board 50 by the housing 30.

C. Other Embodiments

While the present invention has been described with reference to the above embodiments, the present invention is not limited thereto, but may be embodied in various other forms without departing from the gist of the invention. For example, the sensor 20 of the sensor apparatus 10 is not limited to an oxygen sensor, but may be a sensor for detecting the concentration of a particular gas component, such as nitrogen oxides or hydrocarbon, or a sensor for detecting a physical quantity, such as temperature or pressure, of fluid to be measured.

Also, a step of inserting the cable 80 into the cable insertion portion 38 may be before or after the first member 100 and the second member 200 are engaged with each other.

Also, the external terminals 40, the first terminals 60, the second terminals 70, and the core wire end portions 82 of insulated wires of the cable 80 may be of the male type or the female type so long as their connection is possible. Also, the forms of the first member 100 and the second member 200 are not limited to those in the above-described embodiments. For example, both of the first member and the second member may have the form of a container body that functions as an opened container, for constituting the housing through engagement thereof.

DESCRIPTION OF REFERENCE NUMERALS

10: sensor apparatus
20: sensor
30: housing
32: external connector
34: trunk portion
36: engagement portion
38: cable insertion portion
40: external terminal
50: circuit board
51: first board surface
52: second board surface
53, 54: mounting section
55: through hole
56, 57: terminal hole
60: first terminal
70: second terminal
72: engagement portion
75: locking ridge
78: crimp portion
80: cable
82: core wire end portion
83: seal member
85: coating
90: control unit
100: first member
110: lid portion
115: O-ring
120: locking ridge
140: protrusion
142: proximal end portion
148: distal end portion
150: board guide portion
152: groove
160: terminal block locking portion
170: board support portion
172: groove
178: guide
180: terminal support portion
200: second member
210: opening portion
220: locking hole
230: locking ridge
260: guide
270: guide
280: terminal holder
388: cable insertion hole
510: terminal block
512: protrusion
514: groove
540: external-terminal-side terminal block
544: engagement hole
560: first-terminal-side terminal block
564: engagement protrusion

The invention claimed is:

1. A sensor apparatus comprising:
a sensor;
a cable electrically connected to the sensor;
a circuit board electrically connected to the sensor through the cable, drivingly controlling the sensor, and outputting an electric signal generated on the basis of detection result from the sensor; and
a housing accommodating the circuit board;
wherein the housing comprises:
a first member having an external terminal for allowing an external system to be electrically connected to the circuit board, and supporting the circuit board in such a condition that the circuit board is electrically connected to the external terminal, and
a second member into which the cable is inserted and which is engaged with the first member and accommodates the circuit board in cooperation with the first member, and
as a result of engagement between the first member and the second member, the housing establishes an electric connection of the circuit board to the cable.

2. A sensor apparatus according to claim 1, wherein:
the first member has a first terminal electrically connected to the circuit board and allowing the sensor to be electrically connected to the circuit board;
the second member has a second terminal electrically connected to the cable and being engageable with the first terminal; and
as a result of engagement between the first member and the second member, the first terminal and the second terminal are engaged with each other and electrically connected to each other.

3. A sensor apparatus according to claim 2, wherein the first terminal and the second terminal, together with the circuit board, are sealed in the housing in a condition that the first member and the second member are engaged with each other.

4. A sensor apparatus according to claim 2, wherein the first terminal and the second terminal are disposed along a surface of the circuit board in a condition that the first member and the second member are engaged with each other.

5. A sensor apparatus according to claim 2, further comprising a terminal block which holds the external terminal and the first terminal,
wherein the terminal block is locked into engagement with the first member, whereby the external terminal and the first terminal are provided in the first member.

6. A sensor apparatus according to claim 5, wherein:
the first member comprises two protrusions, each provided in a protruding condition and having a proximal end portion and a distal end portion;
the terminal block is held between the two protrusions; and
spacing between the two protrusions is narrower on a side toward the proximal end portions than on a side toward the distal end portions.

7. A sensor apparatus according to claim 5, wherein:
the terminal block is fixed to the circuit board, and
the first member further comprises two board guide portions provided in a protruding condition and adapted to guide the circuit board therebetween.

8. A sensor apparatus according to claim 5, wherein the terminal block comprises:
an external-terminal-side terminal block for holding the external terminal, and
a first-terminal-side terminal block configured as a separate member from the external-terminal-side terminal block and adapted to hold the first terminal.

9. A sensor apparatus according to claim 2, wherein the external terminal and the first terminal are integrally molded to the first member.

10. A sensor apparatus according to claim 2, wherein the first member comprises:
two board support portions provided in a protruding condition and adapted to support the circuit board therebetween, and a terminal support portion provided between the two board support portions in a bridging condition and adapted to support the first terminal.

11. A sensor apparatus according to claim 10, wherein the two board support portions have respective guides for guiding the second member to a position of engagement with the first member.

12. A sensor apparatus according to claim 1, wherein:
the second member is a container body that functions as an opened container, and
the first member is a lid body that functions as a lid of the second member.

* * * * *